United States Patent
Awad

(10) Patent No.: US 6,936,686 B2
(45) Date of Patent: Aug. 30, 2005

(54) CROSS-LINKED SILICONE GELS; PRODUCTS CONTAINING THE SAME; AND METHODS OF MANUFACTURE THEREOF

(75) Inventor: Nagi M. Awad, Franklin Lakes, NJ (US)

(73) Assignee: NuTech Corporation, Newark, NJ (US)

( * ) Notice: Subject to any disclaimer, the term of this patent is extended or adjusted under 35 U.S.C. 154(b) by 0 days.

(21) Appl. No.: 10/646,122

(22) Filed: Aug. 22, 2003

(65) Prior Publication Data

US 2004/0138376 A1 Jul. 15, 2004

Related U.S. Application Data

(60) Provisional application No. 60/432,947, filed on Dec. 11, 2002.

(51) Int. Cl.$^7$ .................................................. C08J 3/24
(52) U.S. Cl. ....................... 528/502 F; 528/31; 528/32; 524/266; 524/268; 524/379; 524/588; 424/486
(58) Field of Search ................... 424/486; 524/266–268, 524/379, 588; 528/31, 32, 502 F, 15; 428/447

(56) References Cited

U.S. PATENT DOCUMENTS

| | | | |
|---|---|---|---|
| 3,159,601 A | 12/1964 | Ashby | |
| 3,159,662 A | 12/1964 | Ashby | |
| 3,220,972 A | 11/1965 | Lamoreaux | |
| 3,715,334 A | 2/1973 | Karstedt | |
| 3,775,452 A | 11/1973 | Karstedt | |
| 3,814,730 A | 6/1974 | Karstedt | |
| 4,374,236 A | 2/1983 | Znaiden | |
| 4,594,134 A | 6/1986 | Hanada et al. | |
| 4,742,142 A | 5/1988 | Shimizu et al. | |
| 4,806,430 A | 2/1989 | Spielvogel et al. | |
| 4,970,252 A | 11/1990 | Sakuta et al. | |
| 4,980,167 A | 12/1990 | Harashima et al. | |
| 4,987,169 A | * 1/1991 | Kuwata et al. | 524/267 |
| 5,061,481 A | 10/1991 | Suzuki et al. | |
| 5,136,068 A | 8/1992 | Bahe et al. | |
| 5,219,560 A | 6/1993 | Suzuki et al. | |
| 5,236,986 A | 8/1993 | Sakuta | |
| 5,266,321 A | 11/1993 | Shukuzaki et al. | |
| 5,412,004 A | 5/1995 | Tachibana et al. | |
| 5,599,533 A | 2/1997 | Stepniewski et al. | |
| 5,654,362 A | 8/1997 | Schultz, Jr. et al. | |
| 5,738,841 A | 4/1998 | Mellul et al. | |
| 5,747,016 A | 5/1998 | Yui et al. | |
| 5,760,116 A | 6/1998 | Kilgour et al. | |
| 5,763,497 A | 6/1998 | Ikeda et al. | |
| 5,783,601 A | 7/1998 | Tanahashi et al. | |
| 5,811,487 A | 9/1998 | Schultz, Jr. et al. | |
| 5,827,509 A | 10/1998 | Richard et al. | |
| 5,849,314 A | 12/1998 | Dobkowski et al. | |
| 5,854,336 A | 12/1998 | Divone et al. | |
| 5,859,069 A | 1/1999 | Yanagida | |
| 5,880,210 A | 3/1999 | Schulz, Jr. et al. | |
| 5,919,468 A | 7/1999 | Bara | |
| 6,027,738 A | 2/2000 | Stepniewski et al. | |
| 6,083,900 A | 7/2000 | Auguste et al. | |
| 6,143,308 A | 11/2000 | Vanstraceele et al. | |
| 6,235,292 B1 | 5/2001 | Bara et al. | |
| 6,331,604 B1 | 12/2001 | Wang et al. | |
| 6,387,405 B1 | 5/2002 | Shah et al. | |
| 6,423,322 B1 | 7/2002 | Fry | |

FOREIGN PATENT DOCUMENTS

| | | |
|---|---|---|
| EP | 0 184 598 | 6/1986 |
| EP | 0 295 886 | 12/1988 |
| EP | 0 545 002 | 8/1992 |
| EP | 0 790 055 | 8/1997 |
| EP | 0 827 983 | 3/1998 |
| WO | 97/44010 | 11/1997 |
| WO | 98/00102 | 1/1998 |
| WO | 98/00103 | 1/1998 |
| WO | 98/00104 | 1/1998 |
| WO | 98/00105 | 1/1998 |
| WO | 98/18438 | 5/1998 |

OTHER PUBLICATIONS

Definition of the word "mill" taken from the Merriam Webster dictionary, tenth ed. p. 739.*

* cited by examiner

Primary Examiner—Margaret G. Moore
Assistant Examiner—Marc S Zimmer
(74) Attorney, Agent, or Firm—Irving M. Fishman

(57) ABSTRACT

A polymerization product of an polyorganohydrosiloxane having a molecular weight of about 3500 to about 4000 and 6–7 Si—H bonds per molecule with a lower alkylene terminated polydimethylsiloxane having a molecular weight of about 20,000 to about 25,000 in the presence of a medium selected from low viscosity silicone oils, hydrocarbon oils typically with the aid of a hydrosilylation catalyst, where the amounts of the siloxanes are chosen such that the reaction product constitutes about 3% to about 15% of the cross-linked polymer and about 97 to about 85% of the reaction medium. The resultant gel is milled in a colloid mill, and if desired, diluted to a concentration of about 3% to about 8% with a diluent selected from the group consisting of low viscosity silicone oil, hydrocarbon oil, lower alkanol, or mixtures thereof. The so produced gel is useable as is or can be formulated into more complex cosmetic formulations having about 65% to about 99.9% of the gel, about 0.1% to about 30% of other non-diluent cosmetic materials (materials that are not low viscosity silicone oil, hydrocarbon oil, or lower alkanol), and up to about 5% lower alkanol.

48 Claims, No Drawings

US 6,936,686 B2

CROSS-LINKED SILICONE GELS; PRODUCTS CONTAINING THE SAME; AND METHODS OF MANUFACTURE THEREOF

CROSS-REFERENCE TO RELATED APPLICATIONS

Priority of U.S. Provisional. Application 60/432,947, filed Dec. 11, 2002 is claimed.

STATEMENT REGARDING FEDERALLY SPONSORED RESEARCH OR DEVELOPMENT

Not Applicable

FIELD OF THE INVENTION

The present invention relates to cross-linked silicone gels where the elastomeric polymer is polymerized in the presence of vehicles selected from low viscosity silicone oils, hydrocarbon oils, or mixtures thereof. The invention further relates to use of particular milling techniques to arrive at the gel of the present invention. The invention also relates to the use of particular polyorganohydosiloxanes and particular alpha, omega—di lower alkenyl terminated polyorganosiloxanes as the polymerization reactants. The invention further relates to cosmetic compositions that utilize the invention gels as the vehicle or as a gellant for compositions containing additional vehicle as well as cosmetically active components. In addition, the invention further applies to the use of the invention gels as dressings for substrates (beyond those of human or animal skin) of a wide variety of natures (inclusive of polymeric and non-polymeric hard surface materials) or as components to formulations for surface treatments for such substrates.

BACKGROUND OF THE INVENTION

Silicone elastomers and silicone gels have been widely used in the cosmetic industry. In many cases such as in the antiperspirant area, gels are produced by adding a gelling agent to the vehicle. In a number of formulations, low viscosity volatile silicone oils (such as cyclomethicones) are used as the vehicle and a gelling agent, typically a solid such as stearyl alcohol and/or hydrogenated castor oil, are added thereto so as to gel the liquid vehicle in the course of formulating the complete product.

In other contexts, polymeric materials that swell in the vehicle, but do not dissolve in it are polymerized and subsequently dispersed in the vehicle. A common problem with such gels is that as dispersions of solid in liquid, they tend to disperse light and therefore yield products that are translucent at best and hazy, cloudy, or even opaque at worst. Such products are also expensive in that they require a substantial amount of the elastomeric material in order to have the desired viscosity. If the concentration is too low (in order to improve clarity), the viscosity is generally unacceptably low for a gel. On the other hand, when the viscosity is in the acceptable range, the clarity of the composition suffers. Typical patents in the field utilizing a dispersion technique include U.S. Pat. No. 6,387,405; U.S. Pat. No. 6,083,900; U.S. Pat. No. 6,027,738; U.S. Pat. No. 5,919,468; and EP 0295886, all of which are incorporated (in their entirety) herein by reference.

Other efforts at improving the viscosity of the silicone gels has focused on the use of silicone resins. In the silicone polymer field, the term resin is generally utilized for silicones having a structure in which a significant number of the silicon atoms are connected to at least three and typically four other silicon atoms via oxygen links. However, when such resins are utilized, they frequently result in cross linked gels that are also unacceptable in that the viscosity and/or clarity are outside of desired limitations. Typical patents relating to silicone resins include U.S. Pat. No. 6,423,322; U.S. Pat. No. 6,143,308; U.S. Pat. No. 5,760,116; U.S. Pat. No. 5,266,321; all of which are incorporated by reference herein in their entirety.

Still other efforts at modification of the elastomeric cross-linked siloxanes have included variations on the addition polymerization reaction of a polyorganohydrosiloxane (a siloxane having Si—H bonds) and an unsaturated polyorganosiloxane. This hydrosilylation reaction is typically carried out in the presence of a catalyst, typically platinum. One variation is to graft alkoxy or alkoxylol groups onto the silicone backbone (U.S. Pat. No. 6,331,604, incorporated herein by reference in its entirety). Another variation has been to use a non-silicone unsaturated molecule to crosslink the polyorganohydrosiloxane or to extend the size of the silicone cross links (U.S. Pat. No. 5,880,210, incorporated herein by reference in its entirety). Yet other variations have been to introduce polyethoxy or polypropoxy or polyethoxy/polypropoxy bridges into the cross-linked polymer (EP 0545002, incorporated herein by reference).

Still further variations on the theme have been to polymerize polyorganohydrosiloxane with unsaturated polyorganosiloxane where the number of reactive groups per molecule in the two reactants is varied or the polymerization reaction is carried out in a different vehicle or a different concentration of vehicle (U.S. Pat. No. 4,970,252; U.S. Pat. No. 4,987,169, both incorporated herein by reference in their entirety).

Notwithstanding all of this activity in the silicone gel area, there have still been difficulties in meeting the needs for a silicone gel having an extremely clear appearance, and a viscosity that is in the appropriate range as well as having an appropriate skin feel, and yet be economical. There have also been difficulties in obtaining the appropriate gel material that can have the above properties and be at a relatively low concentration so as to allow for incorporation of other useful components for various product compositions.

OBJECTS OF THE INVENTION

It is among the objects of the present invention to provide a silicone gel that is crystal clear, and has a high viscosity with relatively little elastomer.

It is another object of the invention to provide a silicone gel that can be made from readily available reactants under easily achievable conditions.

Still other objects of the invention will be recognized by those of ordinary skill in the art.

BRIEF SUMMARY OF THE INVENTION

These and other objects of the invention are surprisingly achieved by a polymerizing an polyorganohydrosiloxane having a molecular weight of about 3500 to about 4000 and 6–7 Si—H bonds per molecule with a lower alkylene terminated polydimethylsiloxane having a molecular weight of about 20,000 to about 25,000 in the presence of a medium selected from low viscosity silicone oils, hydrocarbon oils (typically with the aid of a hydrosilylation catalyst), where the amounts of the siloxanes are chosen such that the reaction product constitutes about 3% to about 15% of the cross-linked polymer and about 97% to about 85% of the reaction medium. During the polymerization reaction, shear is kept to a minimum to allow for the optimal growth of the polymer. The resultant swollen gel is then milled in a colloid mill, and if desired, diluted to a concentration of about 3% to about 8% with a diluent selected from the group consisting of low viscosity silicone oil, hydrocarbon oil, lower alkanol, or mixtures thereof. The so produced gel is useable as is or can be formulated into more complex cosmetic formulations having about 65 to about 99.9% of the gel, about 20% to about 30% of other non-diluent cosmetic materials (materials that are not low viscosity silicone oil, hydrocarbon oil, or lower alkanol), and up to about 5% lower alkanol.

BRIEF DESCRIPTION OF THE DRAWING

Not Applicable.

DETAILED DESCRIPTION OF THE INVENTION

The present invention is a silicone gel, products (primarily cosmetic products) incorporating the gel therein, and methods of making the gel and the cosmetic products made therefrom. The gel per se comprises a cross-linked polysiloxane in an amount of about 3% to about 15% and liquid vehicle that was the polymerization reaction medium in an amount of about 97% to about 85% by weight. The cross-linked polysiloxane is prepared via a hydrosilylation reaction in the presence of a hydrosilylation reaction catalyst in the presence of the stated reaction medium where the reaction medium is selected from the group consisting of low viscosity silicone oils, hydrocarbon oils, and mixtures thereof. Preferably, the reaction takes place in the substantial absence of a hydrosilylation catalyst inhibitor.

Preferably the low viscosity silicone oils are selected from silicone oils having a viscosity of not more than about 200 cps, more preferably not more than about 100 cps, even more preferably not more than about 50 cps, most preferably not more than about 25 cps. These low viscosity silicone oils can be linear, branched, or cyclic, preferably cyclic, even more preferably they are cyclomethicones having 3–7 dialkylsiloxy units, preferably 4–6 such units, more preferably about 5 such units. The dialkyl groups may each independently have up to 3 carbon atoms, but preferably have only 1 or 2, most preferably only 1 carbon atom (methyl), and while they do not have to all be the same, preferably all of the alkyl groups are the same. The most highly preferred of the low viscosity silicone oils is decamethylpentasiloxane (the pentameric form of cyclomethicone). It will be recognized by those of ordinary skill that commercially available cyclomethicones are mixtures of a few different cyclomethicones, generally with one of the forms being predominant and that reference to the "pentameric form" includes the pure pentameric form as well as those commercially available cyclomethicone products that have the pentameric form as the predominant component, preferably the majority component, most preferably substantially the only component thereof. The non-cyclic low viscosity silicones for use as the reaction medium in the present invention include poly dialkylsiloxane that is linear or branched, having up to about 50 Si—O repeating units, preferably up to about 40 such units, more preferably having up to about 30 such units, even more preferably up to about 20 such units, still more preferably up to about 10 units, most preferably up to about 6 units. The alkyl side chains can be up to 3 carbons in length and need not be the same for all of the groups. However, these alkyl side groups are preferably methyl or ethyl and preferably are all the same. Most highly preferred is when all of the alkyl side groups are methyl.

The hydrocarbon oils that are generally useful for the reaction medium in the present invention are saturated liquid hydrocarbons and include, without limitation, those that are straight chain or branched and having 10–18 carbons atoms, for example isodecane, isododecane, isohexadecane, isooctadecane, etc. Isododecane and isohexadecane are preferred materials for the hydrocarbon oils.

As the polymerization catalyst, any hydrosilylation reaction catalyst known in the art may be used, such as chloro platinate (hexavalent platinum) (generally dissolved in 2-propanol or other suitable inert solvent), and zero valent platinum divinyl complex (generally dissolved in vinylsilicone fluid or other suitable inert solvent), with the zero valent platinum divinyl complex being preferred.

The silylation reaction may be run at any desired temperature known to be suitable in the art. However, in order to allow for maximum three dimensional network development, the reaction should be run at low temperature, for example in the range of about 20–about 50° C., preferably at about 20–about 40° C. Reaction times will differ depending upon the temperature and other factors known in the art; however, longer reaction times are preferred for fuller three dimensional network formation. As stated, the silylation reaction should be conducted in the substantial absence of a silylation reaction catalyst inhibitor, preferably in the complete absence of such an inhibitor.

The α,ω-di lower alkenyl terminated polyorganosiloxane is of formula I:

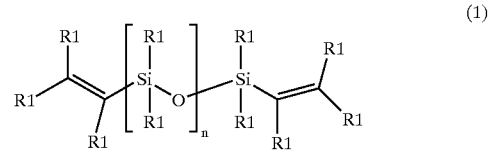

(1)

and has a molecular weight of about 20,000 to about 25,000, (preferably about 21,000 to about 24,000, more preferably about 22,000 to about 23,000, even more preferably about 22,250 to about 22,750, most preferably about 22,400 to about 22,600) with n being about 265 to about 340 (preferably about 275 to about 330, more preferably about 285 to about 320, even more preferably about 295 to about 305, still more preferably about 300) and each R1 being independently H, or an alkyl group of 1 or 3 carbons.

The polyorganohydrosiloxane used in the invention is of formula II:

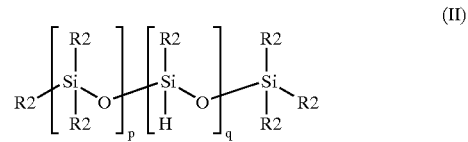

(II)

where the molecular weight of reactant II is about 3500 to 4000 (preferably about 3600 to about 3900, more preferably about 3700 to about 3800, still more preferably about 3725 to about 3775, still more preferably about 3740 to about 3760); q is about 5 to about 9; p is about 40 to about 50, and each R2 is independently an alkyl of 1–3 carbon atoms.

Optionally, the reaction may take place in the presence of a mono-α-olefin or a polyalkoxylated mono-α-olefin to result in grafting onto the resulting polymer the hydrogenated olefin. Use of these "grafts" allows for adjustments in the hydrophilic/hydrophobic nature of the gel. When hydroxyl-terminated α-olefin is utilized (such as that prepared from 1-hydroxy-1-alkynyl compounds and ethylene oxide, propylene oxide, or mixtures thereof), the olefin can cross-link the α,ω-di lower alkenyl terminated polyorganosiloxane since both the unsaturated bond and the hydroxyl group can react with the Si—H bonds of the polyorganohydrosiloxane, allowing further fine tuning of the pore size or voids, which depends upon the relative amount of the hydroxyl-terminated α-olefin and the separation distance of the hydroxyl group from the unsaturated bond therein. Further details on grafting groups onto silicones are disclosed in U.S. Pat. No. 6,331,604, which is incorporated herein in its entirety by reference.

Generally, the reaction medium (the low molecular weight silicones and/or the hydrocarbon oil) is placed in a suitable vessel and the compounds of formulae I and II and any optional olefin are added with mixing. The temperature is generally adjusted to about 20° C. to about 50° C. and the reaction catalyst is added while mixing and shearing forces are now controlled. The control of shearing forces is achieved by allowing for gentle mixing to be continued until visible gelling has taken place (about 5–40 minutes), after which mixing and heating are halted to allow the reaction to proceed without breaking down the gelling matrix. In a preferred method, a small blade (relative to the vessel size) is used for mixing, which because of its smaller size does not move the entire mass simultaneously. This allows for greater variability in the point at which mixing is stopped in that the stopping point is not as critical. Somewhat overshooting the visible gel formation point is acceptable because a substantial portion of the reaction mass is able to extend the polymer network even though the mixing is continuing. Nonetheless, mixing should be stopped shortly afterwards. In a preferred embodiment, the polymerization reaction is conducted in the substantial absence of shearing forces. The gelling reaction is allowed to continue for about at least about 2 hours, preferably at least about 3 hours, more preferably at least about 4 hours and continues until a bouncy gel is formed. Generally, the reaction is complete by about less than 24 hours, but in some cases longer times may be needed.

The resulting bouncy gel is then subjected to a controlled shear to produce a soft paste gel and then optionally (i) diluted with additional amounts of (a) low viscosity silicone oil and/or (b) hydrocarbon oil and/or (c) a lower alkanol and (ii) then subjected to limited shearing. The controlled shearing is accomplished generally by forcing the gel or diluted gel through a colloid mill or Silverson homogenizing head or mixing in a dual or triple shaft mixer or double planetary mixer. In the case of the colloid mill, suitable gap openings are in the range of 10–50 mils, with about 20–30 mils being preferred. Transit time through the mill as well as gap opening are typically adjusted to obtain the desired soft paste gel viscosity. Other shearing techniques that apply controlled shear of the same type may be used as will be apparent to those of ordinary skill in the art. Use of the colloid mill is preferred. The limited shearing is accomplished by mixing the soft paste gel and further diluent in a dual or triple shaft mixer, double planetary mixer, or Hochmeyer heavy duty mixer. The degree of shearing and the amount of diluent are adjusted to obtain the desired viscosity of the end product. Other shearing techniques that apply limited shear of the same type may be used as will be apparent to those of ordinary skill in the art. The resulting soft paste gels (after applying the controlled shear, but before applying the limited shear) have viscosities frequently in excess of 1,000,000 cps, preferably frequently in excess of 2,000,000 cps. After application of the limited shearing, the resultant gels have viscosities less than 2,000,000 cps, have viscosities preferably in the range of up to about 1,500,000 cps, more preferably in the range of up to about 1,000,000 cps, still more preferably up to about 750,000 cps and usually have a viscosity in excess of about 100,000 cps (although lower viscosities in particular instances are possible and within the scope of the invention), preferably in excess of about 150,000 cps. Specific viscosities can be obtained by regulation of the amount of diluent used as well as the degree of shear applied in the limited and/or controlled shearing steps. Particular non-limiting exemplary viscosity ranges within the scope of the present invention include lower limits of about 50,000 cps, about 75,000 cps, about 100,000 cps, about 150,000 cps, about 200,000 cps, about 300,000 cps, about 400,000 cps, etc and upper limits of 2,000,000 cps, about 1,500,000 cps, about 1,250,000 cps, about 1,000,000 cps, about 900,000 cps, about 800,000 cps, about 750,000 cps, etc.

The gel that emerges from the limited shear treatment can now be used with cosmetically useful ingredients to result in is cosmetically useful gel products. Such cosmetic products include virtually any type of cosmetic that contains hydrocarbon and/or silicone solvents needing gelling (by further absorbing at least a portion of the solvent). Cosmetic compositions of the invention also include the incorporation of cosmetically active substances into the gel itself, with or without other cosmetic formulation auxiliaries as may be necessary. Typical cosmetic active substances include antiperspirants, deodorants, fragrances, flavors, sunscreens (such as octocrylene, octyl methoxy cinnamate, octyl salicylate, benzophenone, etc. and blends thereof), moisturizers, among others well known in the cosmetic arts. In general, the compositions in which the gel is used may utilize the gel of the invention as a minor gelling component, or as the primary formulation base. Where the invention gel (about 3% to about 15% polymer and about 97% to about 85% silicone oil or hydrocarbon oil as calculated as the gel emerges from the colloid mill or other light shearing step) is the primary matrix component of the formulation, it is preferably used in amount of about 65 to about 99.9% of the composition (preferably up to about 95%, more preferably up to about 90%, still more preferably up to about 80%), along with about 0 to about 10% of additional diluent selected from low viscosity silicone oils, hydrocarbon oils, and lower alkanols and about 0.1 to about 30% of at least one cosmetically acceptable ingredient which cosmetic ingredient is not a low viscosity silicone oil, a hydrocarbon oil, or a lower alkanol, or mixtures thereof. In addition to cosmetically active ingredients, where desired, the active agent component may also be a suitable pharmaceutically active material, most preferably a topically or transdermally active pharmaceutical active agent.

The resultant gels may also be used for dressings for a wide range of non-skin surfaces, especially for polymeric surfaces such as rubber and plastics, especially rubber, most particularly automotive surfaces, such as tires and other polymeric surfaces. When applied to the surface of tire walls, the gels of the invention form a tough, dry film which results in minimizing the adherence of road dirt (so as to maintain a good tire appearance), reduces or prevents leaching of carbon black from the tire wall (thereby retarding aging of the tire), provides a water resistant barrier against rain and puddles (thereby helping to maintain a newer tire look for longer periods of time). Other rubber or rubber like materials that would benefit from the leaching reduction and the water resistance advantages include articles as diverse as sealing rings, gaskets, for miscellaneous equipment, etc. In addition, the water resistant properties can be suitably used in aiding the sealing or rejuvenating the sealing properties of weatherstripping and caulking etc. Those of ordinary skill in the art will be aware of further applications of the present invention as extensions of those applications set forth herein.

EXAMPLES

The following examples exemplify, but do not limit, the present invention.

Example 1

A gel having the following formulation is prepared as set forth below.

| | |
|---|---|
| 1. α,ω-di vinyl polydimethylsiloxane | 10.38% |
| 2. polymethylhydrosiloxane | 0.822% |
| 3. platinum catalyst | 0.00393% |
| 4. α,ω-di vinyl polydimethylsiloxane | 0.389% |
| 5. isododecane | 88.045% |

Component 3 is pre-blended with component 4. Component 5 and then components 1 and 2 are charged into a reaction vessel and the pre-blend of components 3 and 4 are added thereto. This is then mixed at 24° to 30° C. until gelation begins (5–20 minutes depending upon temperature). The mixing and heating is stopped and the reaction is allowed to go to completion. On completion of the gelling reaction, the product is pumped through a colloid mill rotating at 3750 to 10,000 rpm. The product comes out of the mill as a soft hot (about 50° to about 60° C.) paste. To this paste (45%) additional isododecane (55%) is added and limited shear is applied using a heavy duty, triple blade mixer to result in a gel product having 5.2% polymer and 94.8% isododecane with a viscosity range of from about 150,000 to 600,000 cps.

Example 2

Following the procedure in example 1 except that cyclomethicone is used instead of isododecane, a gel is produced from the following components that may be used as is without the final dilution step in Example 1.

| | |
|---|---|
| 1. α,ω-di vinyl polydimethylsiloxane | 5.19% |
| 2. polymethylhydrosiloxane | 0.411% |
| 3. platinum catalyst | 0.00393% |
| 4. α,ω-di vinyl polydimethylsiloxane | 0.389% |
| 5. pentameric cyclomethicone | 94.005% |

This may be used as is (6% polymer and 94% cyclomethicone) or is further diluted to result in a softer gel by adding an amount of pentameric cyclomethicone equal in weight to the above gel to result in a softer gel having 3% polymer and 97% cyclomethicone with a viscosity range of from about 150,000 to about 800,000 cps.

65 g of the 3% polymer gel product above is blended with 5 g of additional pentameric cyclomethicone and 30 g of hydrogenated polyisobutene and blended to form a suitable product with a viscosity in the range of about 150,000 cps to about 600,000 cps.

Example 3

Following the procedure in Example 1, a gel is prepared having the following reactants:

| | |
|---|---|
| 1a. α,ω-di vinyl polydimethylsiloxane | 6.27% |
| 1b. α,ω-di vinyl polydiphenyldimethylsiloxane | 1.13% |
| 2. polymethylhydrosiloxane | 0.661% |
| 3. platinum catalyst (2%) | 0.0147% |
| 4. α,ω-di vinyl polydimethylsiloxane | 0.2401% |
| 5. pentameric cyclomethicone | 91.69% |

70 g of the resulting soft paste is blended with (a) 25 g of a sunscreen blend and (b) either 5 g of isododecane or 5 g of pentameric cyclomethicone to yield a translucent to clear sunscreen gel or a translucent sunscreen gel respectively.

Example 4

Following the procedures above, gels having polymer and diluent content as set forth below are prepared:

| Gel | Cross-linked Polymer | Amount | Diluent | Amount | Viscosity (cps) |
|---|---|---|---|---|---|
| A. | polydimethylsiloxane | 6% | cyclopentasiloxane | 94% | >2,000,000 |
| B. | polydimethylsiloxane | 6% | cyclotetrasiloxane | 94% | >2,000,000 |
| C. | polydimethylsiloxane | 6% | polydimethylsiloxane (5 cps) | 94% | >2,000,000 |
| D. | polydiphenyldimethylsiloxane | 8% | cyclopentasiloxane | 92% | >2,000,000 |
| E. | polydiphenyldimethylsiloxane | 8% | isododecane | 92% | 1,600,000 |
| F. | polydiphenyldimethylsiloxane | 8% | isohexadecane | 92% | 1,700,000 |
| G. | polydiphenyldimethylsiloxane | 8% | polydimethylsiloxane (5 cps) | 92% | >2,000,000 |
| H. | polydimethylsiloxane | 8% | isododecane | 92% | 1,700,000 |

These gels are then further formulated as set forth below using 70% of the gel along with the recited ingredients.

| Formulation Component | I | II | III | IV | V | VI |
|---|---|---|---|---|---|---|
| Gel | A | B | A | D | E | F |
| Cyclopentasiloxane | 30% | — | 3% | 5% | — | — |
| Cyclotetrasiloxane | — | 30% | — | — | — | — |
| Isododecane | — | — | — | — | 5% | — |
| Isohexadecane | — | — | — | — | — | 5% |
| Hydrogenated Polyisobutene | — | — | 27% | — | — | — |
| Sun Screen Blends* | — | — | — | 25% | 25% | 25% |
| Viscosity (× 1000 cps) | 390 | 300 | 900 | 440 | 450 | 440 |

Example 5

In the foregoing examples, the cross-linked polydimethylsiloxane is prepared from approximately 93% polydimethylsiloxane terminated with ethylene groups (having a molecular weight of about 23,600); approximately 7% polymethylhydrodimethylpolysiloxane (having a molecular weight of about 3756; and approximately 0.06% of zerovalent platinum divinyl complex dissolved in linear vinyl silicone fluid. The cross-linked diphenyldimethylpolysiloxane is prepared from 43.7% diphenyldimethylpolysiloxane terminated with ethylene groups (having a molecular weight of about 18,900); 48.3% polydimethylsiloxane terminated with ethylene groups (having a molecular weight of about 23,600); approximately 7.77% of polymethylhydrodimethylpolysiloxane (having a molecular weight of about 3756); and 0.18% of catalyst containing 2% platinum as a zero valent platinum divinyl complex dissolved in linear vinyl silicone fluid.

I claim:

1. A cross-linked silicone gel substantially free of $SiO_2$ groups, substantially free of $SiO_{1.5}$ groups, and substantially free of polyalkyleneoxide groups, comprising a cross-linked polymerization product of
   (A) (i) an α,ω-di loweralkenyl terminated polyorganosiloxane of formula I

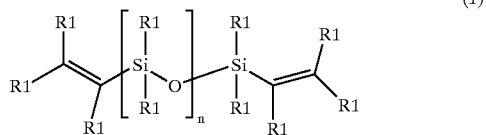

(1)

having a molecular weight of about 20,000 to about 25,000 with n being about 265 to about 340 and each R1 being independently H, or an alkyl group of 1 or 3 carbons and
   (ii) optionally an α,ω-di ethylene terminated polydiphenyldimethylorganosiloxane; and
   (B) a polyorganohydosiloxane of formula II

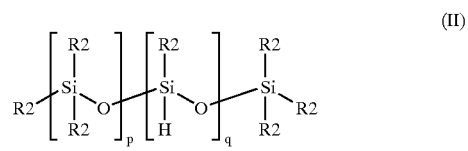

(II)

where the molecular weight of reactant II is about 3500 to 4000; q is about 5 to about 9; p is about 40 to about 50, and each R2 is independently an alkyl of 1–3 carbon atoms;
   said polymerization product being polymerized in the presence of a medium selected from the group consisting of hydrocarbon oils, and mixtures thereof; and
   (C) said medium
      wherein said polymerization takes place initially with mixing and said mixing is halted when gelling is visibly seen.

2. The silicone gel of claim 1 wherein after said polymerization, said gel is subjected to milling, said milling being conducted while said gel is in the swollen state.

3. The silicone gel of claim 2 wherein said milling is conducted in a colloid mill.

4. The silicone gel of claim 1 comprising about 3% to about 15% of said polymer and about 97% to about 85% of said medium.

5. The silicone gel of claim 1 which is further diluted with a diluent selected from the group consisting of hydrocarbon oils, lower alkanols, and mixtures thereof.

6. A cosmetic formulation comprising about 65% to about 99.9% of the silicone gel of claim 1, about 0.1% to about 30% of at least one cosmetically acceptable ingredient which cosmetic ingredient is not a low viscosity silicone oil, a hydrocarbon oil, or a lower alkanol, or mixtures thereof; and up to about 10% of a diluent selected from the group consisting of low viscosity silicone oils, hydrocarbon oils, and lower alkanols.

7. A method of making a clear silicone gel comprising
   (A) (i) polymerizing in the presence of a hydrosilylation polymerization catalyst and a medium selected from the group consisting of hydrocarbon oils, and mixtures thereof
      (1) an α,ω-di lower alkenyl terminated polyorganosiloxane of formula I

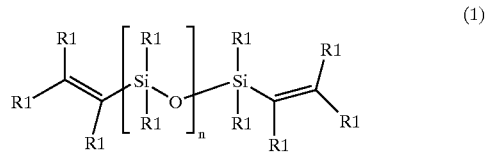

(1)

having a molecular weight of about 20,000 to about 25,000 with n being about 265 to about 340 and each R1 being independently H, or an alkyl group of 1 or 3 carbons and
      (ii) optionally an α,ω-di ethylene terminated polydiphenyldimethylorganosiloxane and
      (2) a polyorganohydrosiloxane of formula II

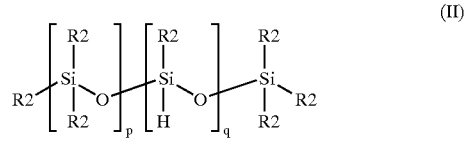

(II)

where the molecular weight of reactant II is about 3500 to 4000; q is about 5 to about 9; p is about 40 to about 50; and each R2 is independently an alkyl having 1–3 carbon atoms resulting in a swollen gel;
   (B) milling said swollen gel; and
   (C) optionally diluting the result of step (B) with a diluent selected from the group consisting of low viscosity silicone oils, hydrocarbon oils, and lower alkanols;
   wherein said polymerization takes place initially with mixing and said mixing is halted when gelling is visibly seen.

8. The process of claim 7 wherein said milling said swollen gel step takes place in a colloid mill.

9. The process of claim 7 wherein said hydrosilylation catalyst is zero valent platinum divinyl complex.

10. The process of claim 7 wherein said polymerization reaction takes place at about 20° C. to about 50° C.

11. The process of claim 7 wherein said reaction is permitted to proceed for at least 2 hours.

12. The process of claim 7 wherein said reaction is permitted to proceed for at least 3 hours.

13. The process of claim 7 wherein said reaction is permitted to proceed for at least 4 hours.

14. The process of claim 7 wherein said polymerization reaction is permitted to take place in the substantial absence of shearing forces.

15. The process of claim 7 further comprising adjusting the viscosity of gel by diluting said gel with a diluent selected from the group consisting of low viscosity silicone oils, hydrocarbon oils, and lower alkanols to result in a diluted gel.

16. The process of claim 15 further comprising passing said diluted gel through a colloid mill.

17. The silicone gel resulting from the process of claim 7, provided that when said optional dilution step (C) of claim 7 is utilized, said diluent is selected from the group consisting of hydrocarbon oils and lower alkanols.

18. The silicone gel of claim 17 wherein said milling said swollen gel step takes place in a colloid mill.

19. The silicone gel of claim 17 further comprising adjusting the viscosity of said gel by diluting said gel with a diluent selected from the group consisting of hydrocarbon oils, and lower alkanols to result in a diluted gel.

20. The silicone gel of claim 19 further comprising passing said diluted gel through a colloid mill.

21. A cosmetic composition incorporating said silicone gel of claim 1.

22. A cosmetic composition incorporating the silicone gel of claim 17.

23. A cosmetic composition incorporating the silicone gel of claim 18.

24. A cosmetic composition incorporating the silicone gel of claim 19.

25. A cosmetic composition incorporating the silicone gel of claim 20.

26. The silicone gel of claim 1 which is substantially clear.

27. The silicone gel of claim 20 which is substantially clear.

28. A method of use of the silicone gel of claim 1 comprising applying said gel to a rubber or rubber-like surface.

29. The method of claim 28 wherein said rubber or rubber-like surface is a member selected from the group consisting of tires, sealing rings, gaskets, weatherstripping, and caulking.

30. The method of claim 29 wherein said rubber or rubber-like surface is an automotive tire.

31. A composition comprising the silicone gel of claim 1 along with components suitable for application to rubber or rubber-like surfaces.

32. A cross-linked silicone gel substantially free of $SiO_2$ groups, substantially free of $SiO_{1.5}$ groups, and substantially free of polyalkyleneoxide groups, comprising a cross-linked polymerization product of (A) (i) an α,ω-di lower alkenyl terminated polyorganosiloxane of formula I

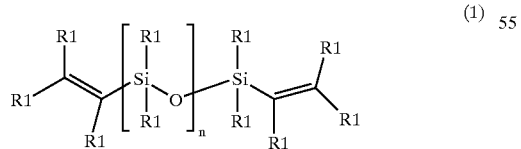

having a molecular weight of about 20,000 to about 25,000 with n being about 265 to about 340 and each R1 being independently H, or an alkyl group of 1 or 3 carbons and (ii) optionally an α,ω-di ethylene terminated polydiphenyldimethylorganosiloxane; and (B) a polyorganohydrosiloxane of formula II

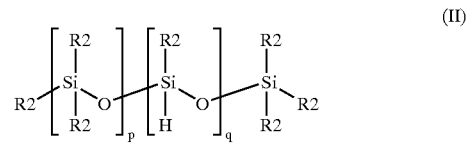

where the molecular weight of reactant II is about 3500 to 4000; q is about 5 to about 9; p is about 40 to about 50, and each R2 is independently an alkyl of 1–3 carbon atoms;

said polymerization product being polymerized in the presence of a medium selected from the group consisting of hydrocarbon oils, and mixtures thereof, and (C) said medium wherein said polymerization reaction is permitted to take place in a manner in which a substantial portion of the reaction mass is not subject to substantial shearing forces.

33. A method of making a clear silicone gel comprising (A) polymerizing in the presence of a hydrosilylation polymerization catalyst and a medium selected from the group consisting of hydrocarbon oils, and mixtures thereof (1) (a) an α,ω-di lower alkenyl terminated polyorganosiloxafle of formula I

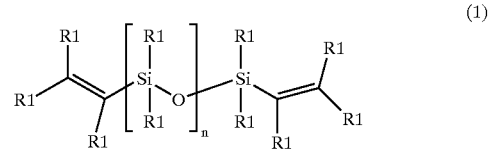

having a molecular weight of about 20,000 to about 25,000 with n being about 265 to about 340 and each R1 being independently H, or an alkyl group of 1 or 3 carbons and (b) optionally an α,ω-di ethylene terminated polydiphenyldimethylorganosiloxane; and (2) a polyorganohydrosiloxane of formula II

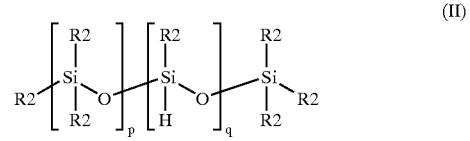

where the molecular weight of reactant II is about 3500 to 4000; q is about 5 to about 9; p is about 40 to about 50; and each R2 is independently an alkyl having 1–3 carbon atoms resulting in a swollen gel;

(B) milling said swollen gel; and (C) optionally diluting the result of step (B) with a diluent selected from the group consisting of low viscosity silicone oils, hydrocarbon oils, and lower alkanols;

wherein said polymerization reaction is pennitted to take place in a manner in which a substantial portion of the reaction mass is not subject to substantial shearing forces.

34. The silicone gel of claim 32 wherein said polymerization reaction is permitted to take place in the substantial absence of shearing forces.

35. The method of claim 33 wherein said polymerization reaction is permitted to take place in the substantial absence of shearing forces.

36. A cross-linked silicone gel substantially free of $SiO_2$ groups, substantially free of $SiO_{1.5}$ groups, and substantially free of polyalkyleneoxide groups, comprising a cross-linked polymerization product of (A) (1) an α,ω-di lower alkenyl terminated polyorganosiloxane of formula I

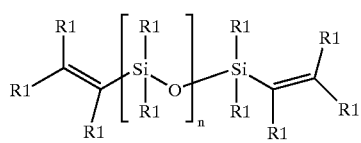

(1)

having a molecular weight of about 20,000 to about 25,000 with n being about 265 to about 340 and each R1 being independently H, or an alkyl group of 1 or 3 carbons;

(2) a member selected from the group consisting of mono-α-olefin, a polyalkoxylated mono-α-olefin, hydroxyl-terminated-α-olefin, and mixtures thereof; and (3) optionally an α,ω-di ethylene terminated polydiphenyldimethylorganosiloxane and (B) a polyorganohydrosiloxane of formula II

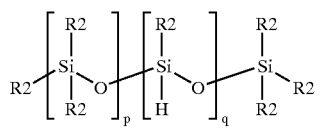

(II)

where the molecular weight of reactant II is about 3500 to 4000; q is about 5 to about 9; p is about 40 to about 50, and each R2 is independently an alkyl of 1–3 carbon atoms;

said polymerization product being polymerized in the presence of a medium selected from the group consisting of low viscosity silicone oils; hydrocarbon oils, and mixtures thereof; and (C) said medium wherein (1) said polymerization takes place initially with mixing and said mixing is halted when gelling is visibly seen or (2) said polymerization reaction is permitted to take place in a manner in which a substantial portion of the reaction mass is not subject to substantial shearing forces.

37. The silicone gel of claim 36 which is further diluted with a diluent selected from the group consisting of low viscosity silicone oils, hydrocarbon oils, lower alkanols, and mixtures thereof.

38. A cosmetic formulation comprising about 65% to about 99.9% of the silicone gel of claim 36 about 0.1% to about 30% of at least one cosmetically acceptable ingredient which cosmetic ingredient is not a low viscosity silicone oil, a hydrocarbon oil, or a lower alkanol, or mixtures thereof; and up to about 10% of a diluent selected from the group consisting of low viscosity silicone oils, hydrocarbon oils, and lower alkanols.

39. A method of making a clear silicone gel comprising (A) polymerizing in the presence of a hydrosilylation polymerization catalyst and a medium selected from the group consisting of low viscosity silicone oil, hydrocarbon oil, and mixtures thereof (1) (a) an α,ω-di lower alkenyl terminated polyorganosiloxane of formula I

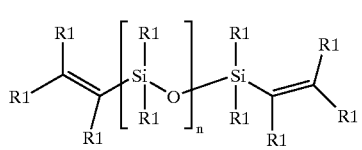

(1)

having a molecular weight of about 20,000 to about 25,000 with n being about 265 to about 340 and each R 1 being independently H, or an alkyl group of 1 or 3 carbons;

(b) a member selected from the group consisting of mono-α-olefin, a polyalkoxylated mono-α-olefin, hydroxyl-terminated-α-olefin, and mixtures thereof; and (c) optionally an α,ω-di ethylene terminated polydiphenyldimethylorganosiloxane and (2) a polyorganohydrosiloxane of formula II

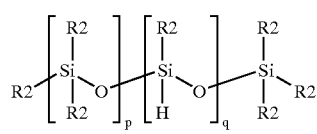

(II)

where the molecular weight of reactant II is about 3500 to 4000; q is about 5 to about 9; p is about 40 to about 50; and each R2 is independently an alkyl having 1–3 carbon atoms resulting in the swollen gel of claim 38;

(B) milling said swollen gel; and (C) optionally diluting the result of step (B) with a diluent selected from the group consisting of low viscosity silicone oils, hydrocarbon oils, and lower alkanols;

wherein (1) said polymerization takes place initially with mixing and said mixing is halted when gelling is visibly seen or (2) said polymerization reaction is permitted to take place in a manner in which a substantial portion of the reaction mass is not subject to substantial shearing forces.

40. The process of claim 39 further comprising adjusting the viscosity of gel by diluting said gel with a diluent selected from the group consisting of low viscosity silicone oils, hydrocarbon oils, and lower alkanols to result in a diluted gel.

41. The silicone gel resulting from the process of claim 39.

42. The silicone gel resulting from the process of claim 40.

43. A cosmetic composition incorporating said silicone gel of claim 36.

44. A cosmetic composition incorporating the silicone gel resulting from the process of claim 39.

45. A cosmetic composition incorporating the silicone gel resulting from the process of claim 40.

46. The silicone gel of claim 36 which is substantially clear.

47. A method of use of the silicone gel of claim 36 comprising applying said gel to a rubber or rubber-like surface.

48. A composition comprising the silicone gel of claim 36 along with components suitable for application to rubber or rubber-like surfaces.

* * * * *